United States Patent [19]
Kobayashi et al.

[11] Patent Number: 5,394,864
[45] Date of Patent: Mar. 7, 1995

[54] BENDABLE PORTION OF ENDOSCOPE

[75] Inventors: Tadasu Kobayashi, Tokyo; Noboru Ujiie, Fukushima; Hirohisa Ueda, Tokyo; Kenichi Ohara, Tokyo; Akira Sugiyama, Tokyo; Ichiro Ninomiya, Tokyo; Hiroshi Sano, Tokyo; Kunitoshi Ikeda, Tokyo, all of Japan

[73] Assignee: Asahi Kogaku Kogyo Kabushiki Kaisha, Tokyo, Japan

[21] Appl. No.: 960,836

[22] Filed: Oct. 14, 1992

[30] Foreign Application Priority Data

Oct. 15, 1991 [JP] Japan .................. 3-266240

[51] Int. Cl.⁶ .............................................. A61B 1/00
[52] U.S. Cl. .......................................... 128/4; 138/124
[58] Field of Search ............... 128/4, 6; 138/124, 126, 138/127, 153

[56] References Cited

U.S. PATENT DOCUMENTS

| | | | |
|---|---|---|---|
| 4,327,711 | 5/1982 | Takagi | 128/4 |
| 4,425,919 | 1/1984 | Alston, Jr. et al. | 138/124 X |
| 4,662,405 | 5/1987 | Besche et al. | 138/124 X |
| 4,676,229 | 6/1987 | Krasnicki et al. | 128/4 |
| 4,870,995 | 10/1989 | Igarashi et al. | 138/124 X |
| 4,944,287 | 7/1990 | Takahashi et al. | |
| 5,125,143 | 6/1992 | Takahashi . | |

FOREIGN PATENT DOCUMENTS

| | | | |
|---|---|---|---|
| 3307185 | 9/1983 | Germany | 128/4 |
| 0154418 | 9/1984 | Japan | 128/4 |
| 4288114 | 10/1992 | Japan | 128/4 |

Primary Examiner—Richard J. Apley
Assistant Examiner—Beverly A. Meindl
Attorney, Agent, or Firm—Sandler, Greenblum & Bernstein

[57] ABSTRACT

A bendable portion which is provided at the distal end of an insert part of an endoscope and bent by remote control. The bendable portion includes an elastic and flexible double walled tube comprising a pair of inner and outer tubes for covering the bendable portion. A device for preventing enlargement of the diameter of the inner tube is sandwiched between the inner and outer tubes.

12 Claims, 5 Drawing Sheets

BENDABLE PORTION OF ENDOSCOPE

BACKGROUND OF THE INVENTION

The present disclosure relates to subject matter contained in Japanese patent application No. 3-266240 (filed on Oct. 15, 1991), which is expressly incorporated herein by reference in its entirety.

1. Field of the Invention

The present invention relates to a bendable portion which is provided at the distal end of an insert part of an endoscope and bent by remote control.

2. Description of the Prior Art

To sterilize or disinfect an endoscope by using ethylene oxide gas or by autoclaving, it is necessary to raise and reduce the pressure in the tank containing the endoscope. Accordingly, the endoscope must be designed to withstand such a pressure change.

The most serious problem that is associated with autoclaving is that a bendable portion covering tube, that is the most flexible of the sheathing members of the endoscope, is inflated and likely to rupture when the pressure in the tank is reduced.

It has been conventional practice to provide a bellows which inflates when the ambient pressure is reduced, or to provide a valve or other similar device in the control part or the light guide connector of the endoscope so as to keep the inside of the endoscope at the same pressure as the ambient pressure, thereby preventing the bendable portion covering tube from rupturing when the pressure in the tank is reduced.

However, the addition of a bellows or a valve device increases the cost of the apparatus. In addition, since the bendable portion covering structure itself is not changed, if the function of the bellows or the valve cannot satisfactorily comply with the reduced pressure conditions, the bendable portion covering tube may rupture.

SUMMARY OF THE INVENTION

An object of the present invention is to provide a pressure-resistant bendable portion of an endoscope wherein the covering structure itself is designed to withstand a change in the environmental pressure so as to prevent rupture of the covering.

Other objects and advantages of the present invention will become apparent from the following detailed description of an illustrated embodiment of the invention.

According to the present invention, there is provided a bendable portion which is provided at the distal end of an insert part of an endoscope and bent by remote control. The bendable portion includes an elastic and flexible double walled tube comprising a pair of inner and outer tubes for covering the bendable portion, and a device for preventing enlargement of the diameter of the inner tube, which is sandwiched between the inner and outer tubes.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
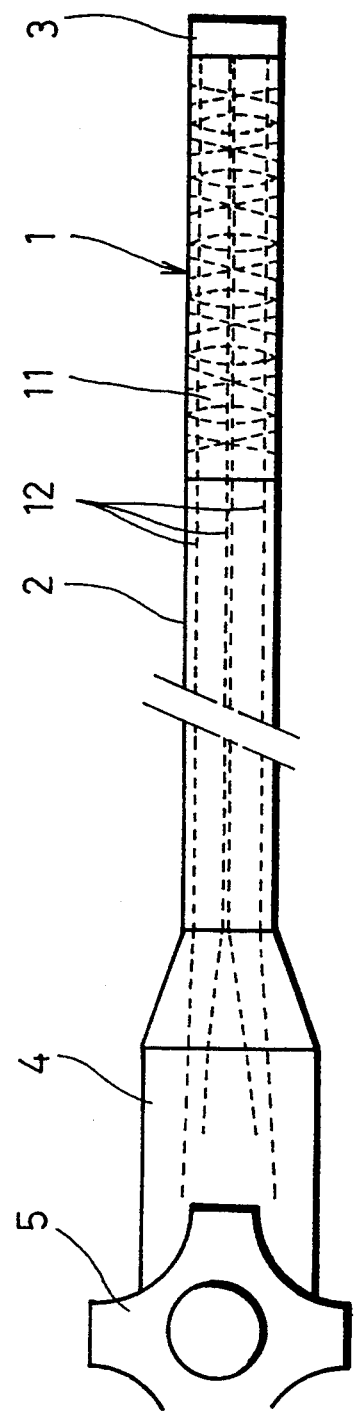
FIG. 1 shows schematically an endoscope according to a first embodiment of the present invention.

Referring to FIG. 1, a bendable portion 1 of an endoscope is connected to the distal end of a flexible insert tube 2 that constitutes an insert part of the endoscope in combination with the bendable portion 1. A distal end block 3 is connected to the distal end of the bendable portion 1. The distal end block 3 incorporates an objective optical system and other necessary components.

A control part 4 is connected to the proximal end of the flexible insert tube 2 and is provided with a bending controller 5 for bending the bendable portion 1 as desired by remote control.

The bendable portion 1 has a bending mechanism which comprises a multiplicity of joint rings 11 pivotably connected in series, and control wires 12 attached at their distal ends to the foremost joint ring 11, so that the bendable portion 1 can be remotely bent by pulling the control wires 12 with the bending controller 5.

Figure 2:
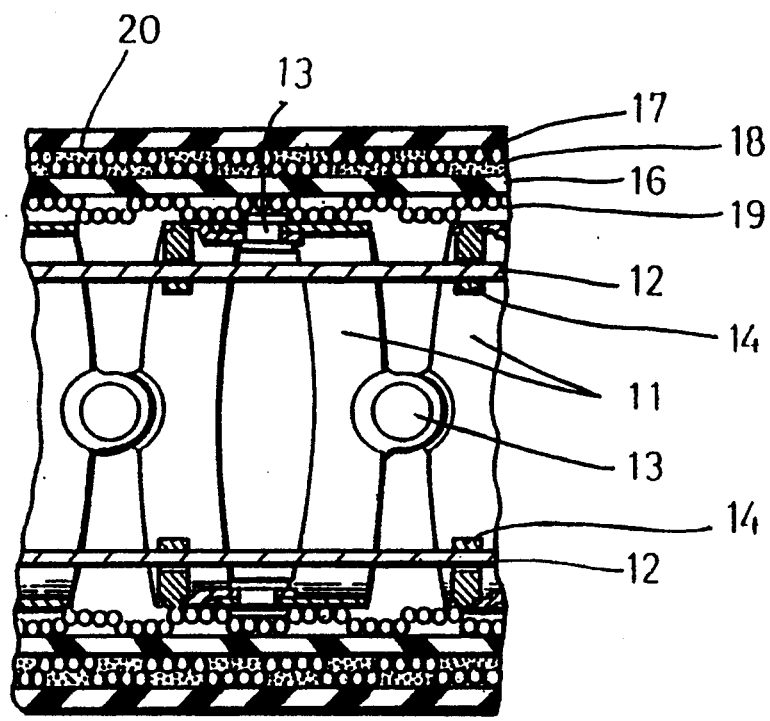
FIG. 2 is a fragmentary sectional view of a bendable portion of the endoscope according to the first embodiment of the present invention.

Referring to FIG. 2, which is an enlarged view of the bendable portion 1, a pair of diametrically opposing rivets 113 pivotally connect together each pair of adjacent joint rings 11 The positions of the rivets 13 are set so that the imaginary line that connects one pair of rivets 13 is at 90 degrees to the imaginary line connecting another pair of rivets 13 which are adjacent to the first pair of rivets 13. Wire guides 14 are rigidly secured to each joint ring 11 to guide the control wires 12.

The outer surface of the train of joint rings 11 is covered with an elastic and flexible double walled tube comprising an inner tube 16 and an outer tube 17. These tubes 16 and 17 may be formed by using, for example, silicone rubber or fluororubber. However, it is not necessary to form both the tubes 16 and 17 of the same material.

It is preferable to use a material having excellent slip properties for the outer tube 17 because it comes in direct contact with a mucous membrane or other parts when the bendable portion 1 is inserted into a cavity of the body. It is also preferable to form the outer tube 17 of a material having excellent watertightness with a view to preventing contamination of a first braid 18 that is sandwiched between the two tubes 16 and 17. The inner tube 16 is preferably formed by using a material having excellent airtightness and pressure resistance.

The first braid 18 is sandwiched between the inner and outer tubes 16 and 17. In addition, a second braid 19 is disposed between the inner surface of the inner tube 16 and the outer peripheral surface of the train of joint rings 11.

Figure 3:
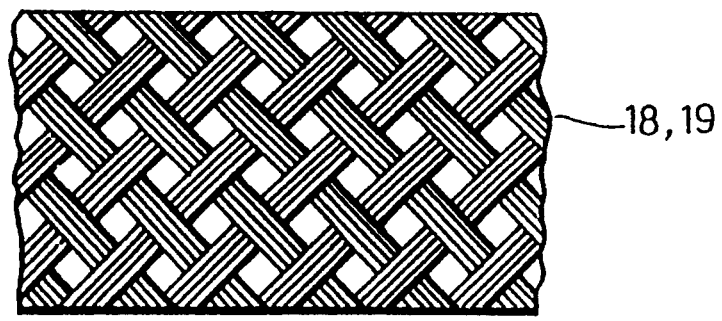
FIG. 3 is a side view of a braid of the endoscope according to the first embodiment of the present invention.

The first and second braids 18 and 19 are tubular members which are formed by coarsely braiding fine strands of metallic or synthetic resin having a diameter in the range of about 0.05 mm to 0.1 mm, for example. More specifically, flat fine strand bundles, which are each formed by arranging a plurality of parallel fine strands in a plane, are braided with a gap provided between each pair of adjacent bundles, as shown in FIG. 3.

However, it is desirable, in order to allow the tubes 16 and 17 to withstand autoclaving, that the mesh size of the braids 18 and 19 should be so small that neither of the tubes 16 and 17 will rupture, even if the pressure inside the inner tube 16 becomes higher than the pressure outside the outer tube 17 by 3 atmospheres.

It should be noted that either of the braids 18 and 19 may be formed by braiding a mix of fine strands of different materials, e.g., metallic strands and synthetic resin strands. That is, both the braids 18 and 19 need not be made of the same material.

A lubricant 20 is sealed in the space between the inner and outer tubes 16 and 17 so as to fill the meshes of the first braid 18. Examples of the lubricant 20 are a powder lubricant such as molybdenum disulfide and a liquid lubricant such as oil. It is also possible to use a gel lubricant.

By filling the space between the inner and outer tubes 16 and 17 with the lubricant 20, the bending operation of the bendable portion 1 can be made light and smooth. However, it is preferable in order to allow the tubes 16 and 17 to withstand autoclaving, to use as the lubricant 20 a heat-resistant liquid lubricant which can be used normally at a temperature of about 135° C.

Thus, the bendable portion 1 is doubly covered with the inner and outer tubes 16 and 17 in a gastight fashion. Further, the first braid 18 is sandwiched between the inner and outer tubes 16 and 17. In addition, the lubricant 20 is sealed in the space between the tubes 16 and 17.

Figure 4:
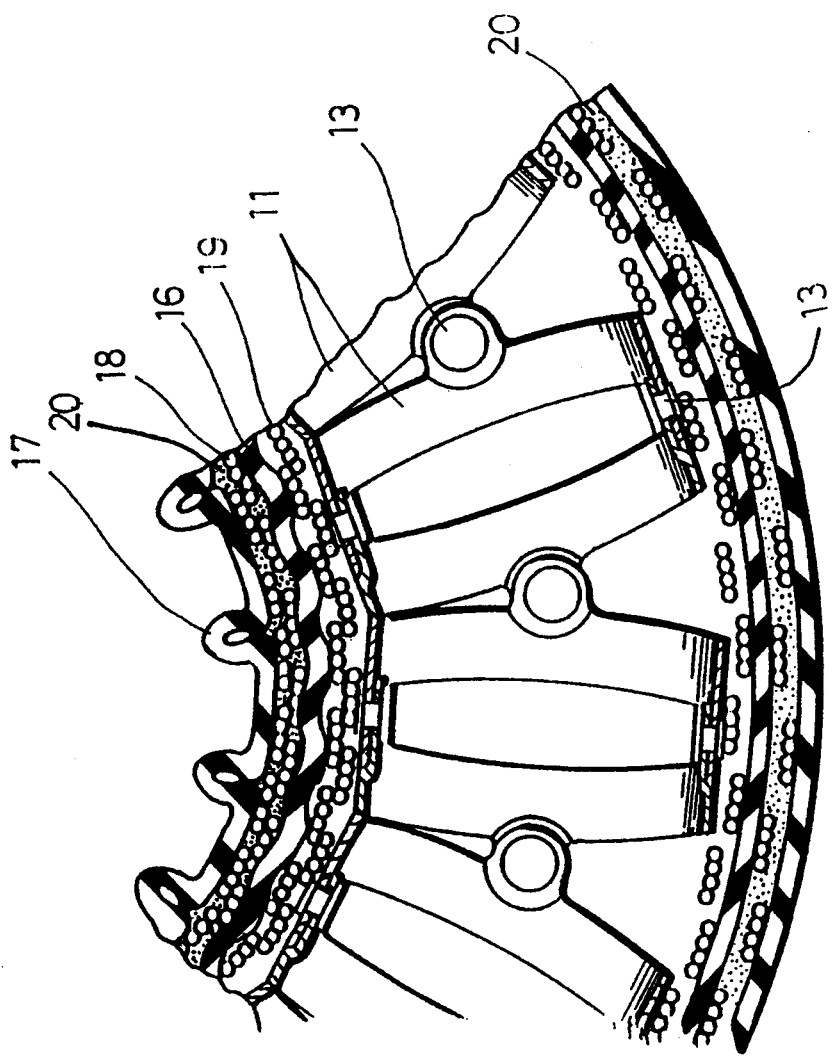
FIG. 4 is a fragmentary sectional view of the bendable portion of the endoscope according to the first embodiment of the present invention.
Figure 5:
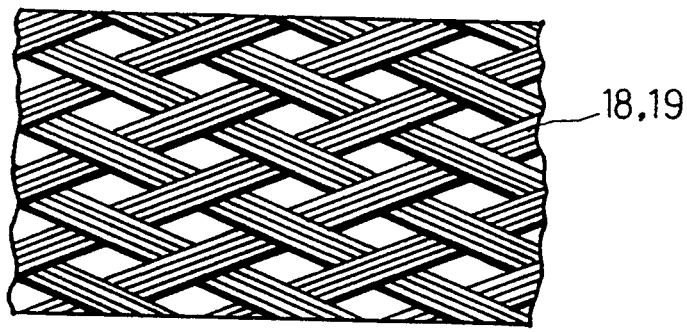
FIG. 5 is a side view of the braid of the endoscope; in an expanded condition, according to the first embodiment of the present invention.
Figure 6:
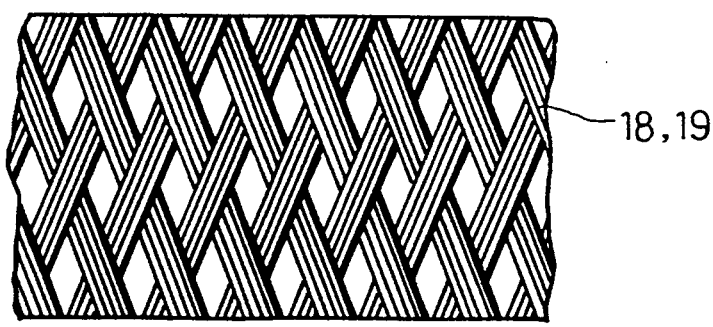
FIG. 6 is a side view of the braid of the endoscope in a compressed condition, according to the first embodiment of the present invention.

When the bendable portion 1 is bent by pulling the control wires 12, as shown in FIG. 4, the braided strands in the convexly curved portions of the braids 18 and 19 are expanded so as to extend in directions close to the direction of the axis, as shown in FIG. 5, whereas the braided strands in the concavely curved portions of the braids 18 and 19 are compressed so as to intersect the axis at angles close to 90 degrees, as shown in FIG. 6. Accordingly, in both the braids 18 and 19, a change in the shape thereof is effectively absorbed by the change of the braiding angle. Thus, the braids 18 and 19 offer no resistance to the bending operation.

In addition, the inner and outer tubes 16 and 17 expand at their convexly curved portions and contract at their concavely curved portions. Thus, the tubes 16 and 17 offer no resistance to the bending operation. Accordingly, the bendable portion 1 can be bent without substantial resistance by remote control from the control part 4.

When the endoscope, arranged as described above, is placed in the tank of an autoclave and the pressure in the tank is raised to a high level, high pressure is applied to the bendable portion 1 from the outer side toward the inner side thereof, so that the outer tube 17 would otherwise be crushed inwardly. However, the applied pressure is first received by the first braid 18 and then received by the second braid 19. Finally, the pressure is received by the outer peripheral surface of the train of joint rings 11. Accordingly, neither of the tubes 16 and 17 will be crushed.

When the pressure in the autoclave tank is reduced to a low level close to a vacuum, the pressure of air in the endoscope acts on the inner tube 16 so as to inflate it.

However, when the inner tube 16 slightly inflates, it is pressed against the first braid 18 and cannot inflate any more. If there is air in the space between the inner and outer tubes 16 and 17, the air expands to inflate the outer tube 17. However, the inflation of the outer tube 17 is slight. If the space between the two tubes 16 and 17 is filled completely with a liquid lubricant or the like, the outer tube 17 will not inflate.

Accordingly, even if the pressure in the autoclave tank is reduced to a low level close to a vacuum, neither of the inner and outer tubes 16 and 17 will rupture by inflation.

It should be noted that the present invention is not necessarily limited to the above-described embodiment. For example, the braids 18 and 19 may be arranged as desired, provided that each of them is formed by coarsely braiding fine strands into a tubular shape. That is, the braids 18 and 19 may be formed by coarsely braiding single strands in place of bundles of strands.

According to the present invention, the bendable portion is covered with a double walled tube comprising a pair of inner and outer tubes, and a braid is sandwiched between the two tubes. Thus, the covering of the bendable portion will not be damaged even by an extreme change in the environmental pressure. Moreover, since the bendable portion covering structure itself has pressure resistance, the durability is reliable and stable. In addition, the structure is simple, and there is substantially no increase in the force required for the bending operation.

In the present invention, it is only necessary for the member that is provided in between the inner and outer tubes 16 and 17 to be capable of preventing enlargement of the diameter of the inner tube 16 without impairing the bendability of the bendable portion 1.

Figure 7:
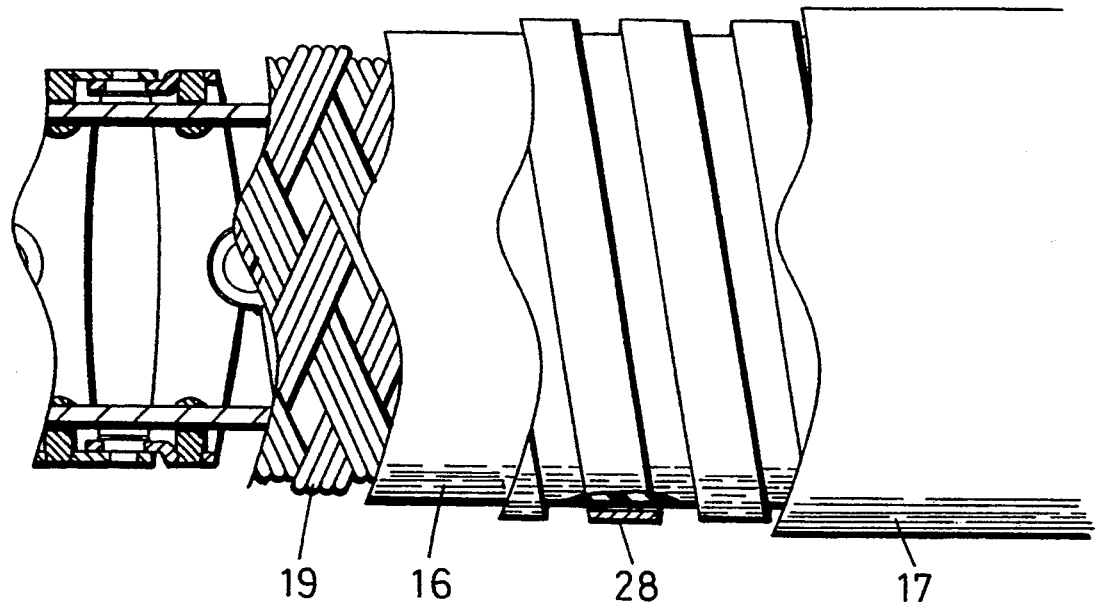
FIG. 7 is a fragmentary sectional view of a second embodiment of the present invention.
Figure 8:
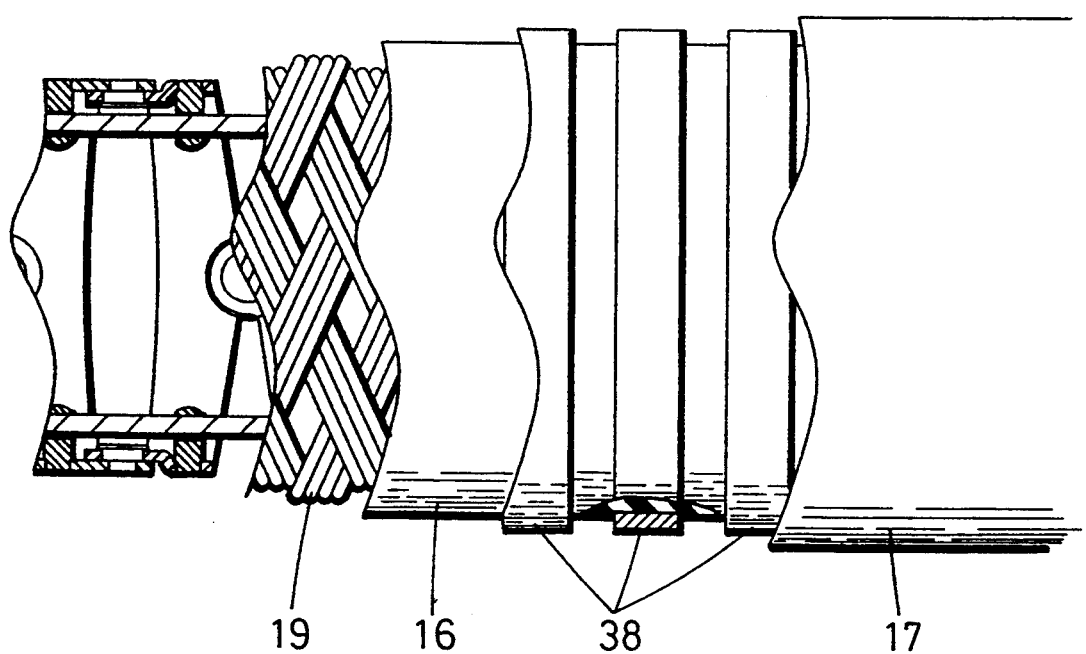
FIG. 8 is a fragmentary sectional view of a third embodiment of the present invention.

Accordingly, the first braid 18 may be replaced, for example, with a spiral tube 28 (second embodiment), as shown in FIG. 7. Alternatively, the first braid 18 may be replaced with a plurality of spaced rings 38, which are disposed to bite into the outer side of the inner tube 16 (third embodiment), as shown in FIG. 8.

Further, the present invention may be applied not only to the bendable portion 1 but also to any other portion of the insert part, for example, the flexible insert tube 2.

While the invention has been described by reference to a specific embodiment chosen for purposes of illustration, it should be apparent that numerous modifications could be made thereto by those skilled in the art without departing from the basic concept and scope of the invention.

We claim:

1. A bendable portion which is provided at a distal end of an insert part of an endoscope and bent by remote control, said bendable portion comprising:
   an elastic and flexible double walled tube comprising a pair of inner and outer tubes for covering said bendable portion, said pair of inner and outer tubes forming a sealed space therebetween;

a tubular member for preventing enlargement of a diameter of said inner tube, said tubular member being sandwiched in said sealed space between said inner and outer tubes, said tubular member being formed with a plurality of gaps, and a lubricant in said gaps in said sealed space between said inner and outer tubes; and a braid provided inside said inner tube, said braid being formed by coarsely braiding fine strands into a tubular shape.

2. A bendable portion of an endoscope according to claim 1, wherein said lubricant is a heat-resistant liquid lubricant.

3. A bendable portion of an endoscope according to claim 1, wherein said tubular member is a spiral tube, said gaps being formed between portions thereof.

4. A bendable portion of an endoscope according to claim 1, wherein said tubular member comprises a plurality of spaced rings, said gaps being formed between respective rings.

5. A bendable portion which is provided at a distal end of an insert part of an endoscope and bent by remote control, said bendable portion comprising:

an elastic and flexible double walled tube comprising a pair of inner and outer tubes for covering said bendable portion, said pair of inner and outer tubes forming a sealed space therebetween;

a braid for preventing enlargement of a diameter of said inner tube, said braid being sandwiched in said sealed space between said inner and outer tubes, said braid being formed by coarsely braiding fine strands into a tubular shape, and by braiding flat fine strand bundles, each braid being formed by arranging a plurality of parallel fine strands in a plane, with a gap provided between each pair of adjacent bundles, and a lubricant in said sealed space between said inner and outer tubes; and a second braid provided inside said inner tube, said second braid being formed by coarsely braiding fine strands into a tubular shape.

6. A bendable portion of an endoscope according to claim 5, wherein said lubricant is a heat-resistant liquid lubricant.

7. A bendable portion which is provided at a distal end of an insert part of an endoscope and bent by remote control, said bendable portion comprising:

an elastic and flexible double walled tube comprising a pair of inner and outer tubes for covering said bendable portion, said pair of inner and outer tubes forming a sealed space therebetween; and a spiral tube for preventing enlargement of a diameter of said inner tube, said spiral tube being sandwiched in said sealed space between said inner and outer tubes, said spiral tube being formed with a plurality of gaps between portions thereof, and a lubricant in said gaps in said sealed space between said inner and outer tubes.

8. A bendable portion of an endoscope according to claim 7, further comprising a braid provided inside said inner tube, said braid being formed by coarsely braiding fine strands into a tubular shape.

9. A bendable portion of an endoscope according to claim 7, wherein said lubricant is a heat-resistant liquid lubricant.

10. A bendable portion which is provided at a distal end of an insert part of an endoscope and bent by remote control, said bendable portion comprising:

an elastic and flexible double walled tube comprising a pair of inner and outer tubes for covering said bendable portion, said pair of inner and outer tubes forming a sealed space therebetween; and a plurality of spaced rings for preventing enlargement of a diameter of said inner tube, said plurality of spaced rings being sandwiched in said sealed space between said inner and outer tubes, said plurality of spaced rings being formed with a plurality of gaps between respective rings, and a lubricant in said gaps in said sealed space between said inner and outer tubes.

11. A bendable portion of an endoscope according to claim 10, wherein said lubricant is a heat-resistant liquid lubricant.

12. A bendable portion of an endoscope according to claim 10, further comprising a braid provided inside said inner tube, said braid being formed by coarsely braiding fine strands into a tubular shape.

* * * * *